(12) United States Patent
Much

(10) Patent No.: US 7,850,365 B1
(45) Date of Patent: Dec. 14, 2010

(54) TOROIDAL CONVECTION MIXING DEVICE

(76) Inventor: Alan Maxwell Much, St. Petersburg, FL (US); Carolyn Much, legal representative, 810 22$^{nd}$ St. North, St. Petersburg, FL (US) 33713

( * ) Notice: Subject to any disclaimer, the term of this patent is extended or adjusted under 35 U.S.C. 154(b) by 0 days.

(21) Appl. No.: 12/503,889

(22) Filed: Jul. 16, 2009

(51) Int. Cl.
B01F 13/02 (2006.01)

(52) U.S. Cl. .................. 366/101; 261/77; 435/296.1

(58) Field of Classification Search .......... 366/101, 366/106, 107, 167.1, 173.1, 173.2, 174.1, 366/175.2; 119/263; 210/416.1–416.5; 261/76–77; 435/296.1

See application file for complete search history.

(56) References Cited

U.S. PATENT DOCUMENTS

| | | | | |
|---|---|---|---|---|
| 2,744,065 A | * | 5/1956 | Lacey | 261/36.1 |
| 4,957,623 A | * | 9/1990 | Henzlik | 210/167.23 |
| 5,190,647 A | * | 3/1993 | Balestrieri | 210/167.26 |
| 7,363,878 B2 | * | 4/2008 | McRobert | 119/259 |
| 2009/0303829 A1 | * | 12/2009 | Muecke | 366/101 |

OTHER PUBLICATIONS

Treece, D., et al., Laboratory Manual for the Culture of Penaeid Shrimp Larvae, TAMU-SG, 1988, vol. 88, No. 202, pp. 35-47.

* cited by examiner

Primary Examiner—Charles E Cooley
(74) Attorney, Agent, or Firm—Ronald E. Smith; Smith & Hopen, P.A.

(57) ABSTRACT

A device for circulating a liquid media in a vessel includes a gas infusion tube having a leading end immersed in the liquid media and a trailing end in fluid communication with a remote air pump. A diffuser is secured to the leading end of the gas infusion tube. The lumen of an outer tube receives the gas infusion tube and the diffuser. The outer tube has a leading end disposed in spaced relation to a bottom wall of the vessel and has a trailing end substantially flush with a level of the liquid media. A plurality of circumferentially spaced openings are formed in the trailing end of the outer tube or in a cap secured to the trailing end. Bubbles are emitted from the diffuser, entraining the liquid media so that it follows a toroidal path of travel that maximizes cell growth.

10 Claims, 3 Drawing Sheets

TOROIDAL CONVECTION MIXING DEVICE

BACKGROUND OF THE INVENTION

1. Field of the Invention

This invention relates to the mixing and gasification of a liquid in a vessel.

2. Description of the Prior Art

Liquid suspensions are conventionally prepared in microbial, chemical, and manufacturing applications by combining a variety of ingredients into narrow-necked vessels such as flasks or carboys. Mixing is required initially to distribute and dissolve the ingredients when preparing a suspension. After initial preparation, mixing is usually required on a continuous basis to maintain the suspension in a homogeneous state.

Bacteria and algae are routinely grown in nutrient solutions in flasks or carboys in microbiological applications. The liquid media include a wide variety of ingredients. Aeration or gasification is often required for optimal growth of the culture. Continuous mixing of the liquid in the vessel is essential to ensure homogeneity of the media, circulation of nutrients, prevention of settling, infusion of gases and, in the case of photosynthetic cultures, equalizing cell access to illumination.

The need for mixing and aeration in a microbial culture growing in a liquid has been conventionally addressed by attaching an aeration tube to a low pressure pump and immersing the tube into the vessel.

Prior art systems teach a bubbling method for liquids in vessels with microalgal culture. This conventional method of inserting an aeration tube to achieve mixing produces air bubbles that rise haphazardly and unevenly in the culture vessel, i.e., the air bubbles do not circulate the liquid media in a consistent pattern. The lack of consistency in mixing inhibits growth of the culture due to non-uniformity of cell access to nutrition, aeration, infused gases, and illumination, i.e., the absence of sustained efficient mixing and continuous patterned circulation within the vessel prevents the attainment of optimal results.

Since ongoing mixing is essential for optimal growth of many microbial cultures, mechanical shakers and stirrers are often employed in lieu of bubblers. These devices are expensive, energy-intensive, and do not incorporate the infusion of gases. Accordingly, they often fail to circulate the deeper levels of the liquid media and otherwise fail to provide energy-efficient, inexpensive optimal circulation.

In areas of applied and industrial chemistry, absorption of gases such as oxygen, chlorine, sulfur, or hydrogen into a liquid often represents a critical step in producing a chemical reaction. Bubble columns, vortex reactors, venturi scrubbers, trickle bed reactors, spray columns, and the like may be used to achieve gas-liquid reactions in a solution. Each of these options represents a substantial capital investment.

There is a need, therefore, for a mixing apparatus that consumes less energy than conventional devices, is less expensive to manufacture, that incorporates the infusion of gases into its functionality, and that creates a flow pattern that continually lifts the bottom layer of the culture to the top of the vessel.

There is also a need for a mixing apparatus having no mechanical moving parts of the type found in mechanical mixing devices.

The needed device would have utility in manufacturing and food processing, such as fermentation, carbonation, hydrogenation, steam injection, and pH control.

However, in view of the prior art taken as a whole at the time the present invention was made, it was not obvious to those of ordinary skill how the identified needs could be fulfilled.

SUMMARY OF THE INVENTION

The long-standing but heretofore unfulfilled need for an inexpensive, low-energy consumption apparatus that efficiently mixes liquid culture media is now met by a new, useful, and non-obvious invention.

The novel device fits into a narrow-necked vessel, such as a flask, half gallon, gallon, or carboy. However, the novel device works equally well with wide-neck or no-neck containers; narrow neck vessels are mentioned because they are in widespread use and most liquid culture media is contained in such vessels.

The novel device simultaneously performs several functions such as mixing, circulation, aeration, and gasification as needed. Its energy consumption is substantially equal to or less than the energy used by conventional devices for bubbling alone.

Filtered air is pumped by a high-volume, low-pressure pump into the vessel. Fluid communication is provided between the pump and vessel by an air infusion tube. The air infusion tube has a distal free end submerged within the vessel. More particularly, the lowermost end of the air infusion tube is not positioned at the bottom of the vessel as in prior art bubbling devices. Instead, it may be positioned near the surface of the media.

A second tube has a larger diameter than the air infusion tube. Said second tube extends from the liquid surface to a predetermined depth so that its lowermost end is positioned close to the bottom of the vessel.

The air infusion tube is disposed within the lumen of the second tube. Accordingly, in this tube-in-tube arrangement, the air infusion tube is the inner tube and the second tube is the outer tube.

A diffuser is mounted to the lowermost end of the inner tube. The diffuser disperses bubbles that lift the liquid media as the bubbles rise. The outer tube extends close to the bottom of the vessel but the inner tube is substantially shorter as aforesaid. The infusion of air via the diffuser creates a vacuum at the bottom of the outer tube. The lifting action raises the liquid inside the outer tube to openings formed in the outer tube located near the surface level of the liquid.

The rising liquid is dispersed in a circular pattern through the openings formed around the top of the outer tube. The air-lift action, created by the diffuser and the vacuum working in tandem, produces a continuous toroidal convection characterized by vertical lifting and lateral dispersal. The liquid from the bottom of the vessel is raised to the top and spouts radially outward in a circular pattern across the liquid surface, simulating a low pressure fountain.

The diffuser is powered by a conventional aquarium-type pump. It continuously produces rising bubbles within the outer tube, thus creating an ongoing lifting motion of the liquid. The resulting action mixes the liquid thoroughly, but gently, circulates the contents vertically and radially in an even pattern, and infuses air and gases, all at the same time. The continuous circulation prevents settling of organisms and ingredients in the media. The uniformity of the media is continuously maintained throughout the vessel.

It is essential to provide equal access to illumination to all cells in a photosynthetic culture. It has been recognized for many decades that significant increase in cell growth of microalgae can be achieved by mixing cultures during growth so that cells can move in and out of high light intensity. Whereas only the outer ten percent (10%) of the culture volume would normally absorb the bulk of the illumination normally positioned in proximity to the vessel, the novel device enables the entire culture to receive uniform access to light by means of an efficient vertical and radial circulatory action. The rising bubbles from the diffuser at the bottom end of the inner tube work in tandem with the vacuum created at the bottom of the open-ended outer tube. The media is continuously lifted from the bottom of the vessel to the top and then circulated around the vessel. Continuous circulation that exposes all parts of the culture to the light source becomes even more critical as the density of the culture increases. The movement of the culture achieved by the novel device remedies the limitation of light penetration that routinely occurs when photosynthetic microbial cultures reach high density.

Uniform continuous mixing of the cultures is essential for aeration, circulation of $CO_2$, nutrient distribution, and exposure to light. To consistently achieve high density culture, the novel device fulfills the mixing requirement, speeds growth, and boosts density in liquid cultures in an energy-efficient manner. The device increases the potential for higher cell concentrations, i.e., higher yield, in the same vessel without altering the media components or growth parameters.

The energy required to achieve thorough carboy mixing and gas infusion using the current invention is the same or less energy as has been consumed by prior art devices to achieve bubbling alone. This invention is an efficient and less expensive alternative to laboratory shakers, stirrers, reactors, or bubble columns.

A primary object of this invention is to provide an inexpensive, energy-efficient device that does a better job of mixing liquid culture media than conventional bubblers and mechanical shakers or stirrers.

Closely related objects include accomplishing the primary object while increasing the potential for higher yield cultures by providing enhanced aeration, circulation, $CO_2$ circulation, nutrient distribution, and exposure to light.

These and other important objects, advantages, and features of the invention will become clear as this description proceeds.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
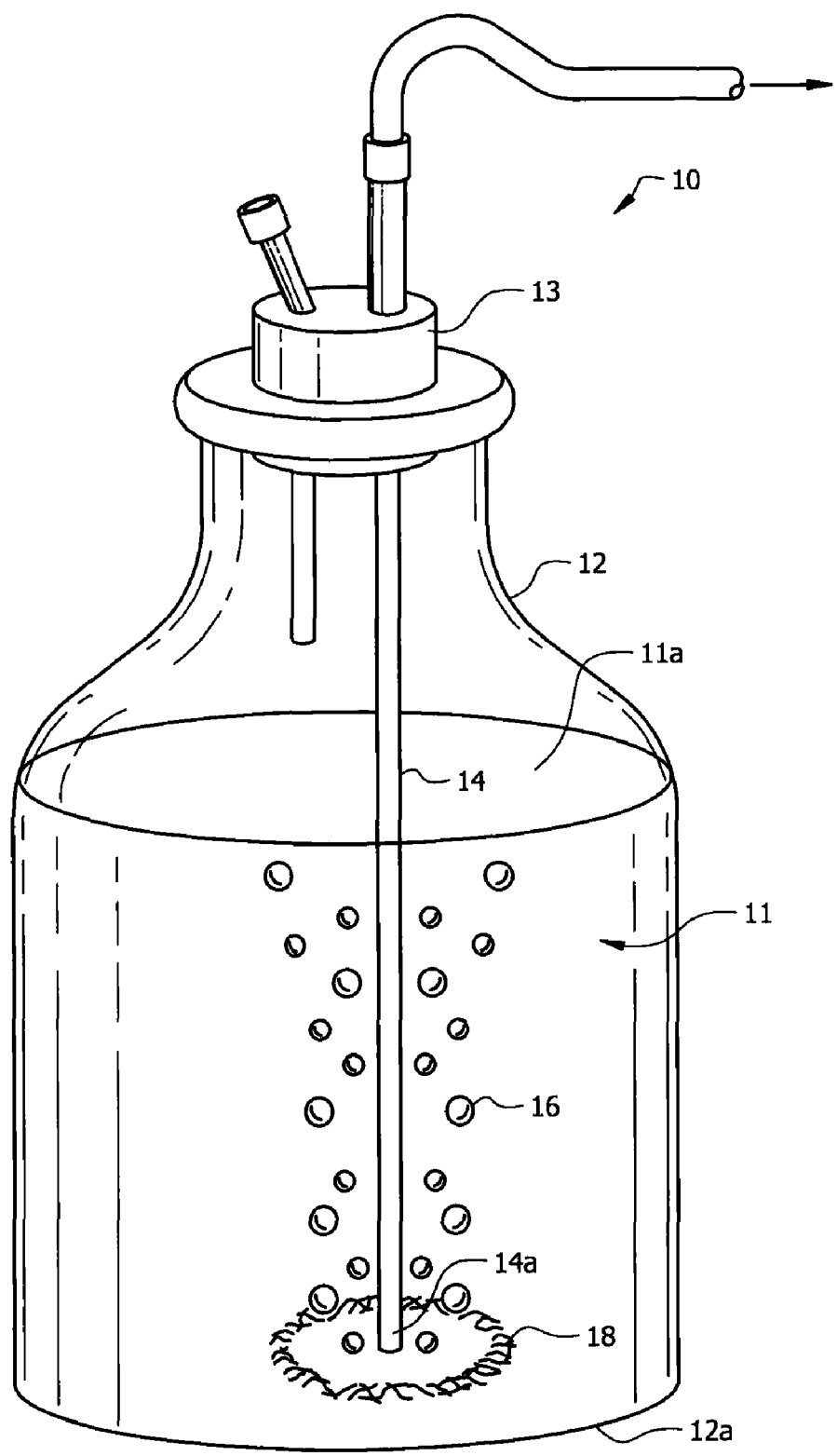
FIG. 1 is a front elevational view of a prior art device.

Referring first to prior art FIG. 1, it will there be seen that a prior art device is denoted as a whole by the reference numeral 10. Device 10 includes vessel 12 that preferably has a narrow neck so that it may be plugged with a stopper having plural bores formed in it. A first bore is needed to admit a tube into the vessel and a second bore is needed to provide a vent. Vessels having narrow necks that are closed with plugs having bores formed therein are of course well-known. A liquid culture media 11 having surface 11a is contained within vessel 12.

In FIG. 1, air infusion tube 14 has a trailing end in fluid communication with a pump, not shown, external to vessel 12. The bottom or leading end 14a of air infusion tube 14 is positioned in abutting relation to bottom wall 12a of vessel 12. When the remote pump is activated, bubbles 16 are created in liquid culture media 11 due to the very close proximity between leading end 14a of tube 14 and bottom wall 12a of vessel 12. Bubbles 16 rise as depicted, thereby providing at least some mixing action in the vessel as said bubbles entrain the liquid culture media, thereby causing said liquid to rise as well.

Reference numeral 18 indicates an undesirable ring of algae that typically forms when this prior art mixing operation is underway.

Pressure of course increases with depth so the pump draws more energy when leading end 14a of tube 14 is submerged to its maximum extent than it would if the tube were not submerged as deeply. However, if tube 14 is elevated so that leading end 14a is spaced apart from bottom wall 12a of vessel 12, the circulation effect created by bubbles 16 is unacceptably lessened.

This prior art arrangement, although not very satisfactory, has been the standard for several decades.

Figure 2:
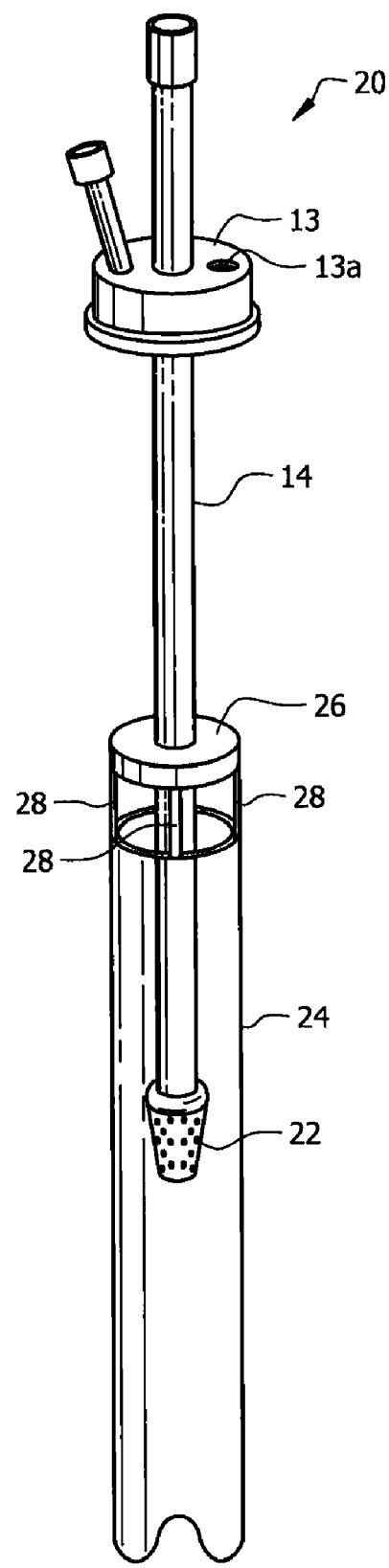
FIG. 2 is a front elevational view of the novel tube-in-tube arrangement.

Referring now to FIG. 2, it will there be seen that an illustrative embodiment of the invention is denoted as a whole by the reference numeral 20. As in the prior art, the preferred vessel 12 has a narrow neck for ease-of-plugging purposes and said vessel contains a liquid culture media 11 having surface 11a. Sample port 13a enables the extracting of samples from a culture without removing stopper 13.

Inner tube 14 is an air infusion tube as in the prior art and has a trailing end in fluid communication with a remote low pressure, high volume filtered air pump as in the prior art.

Diffuser 22 is mounted in capping relation to submerged or leading end 14a of said inner tube. Diffuser 22 causes the filtered air flowing out of said submerged, leading end 14a to be broken up into a large quantity of bubbles 16 as depicted. In an embodiment of the invention diffuser 22 is constructed of frittered glass which may be autoclaved. These diffuser-emitted bubbles act much like prior art bubbles 16 but they are spaced much higher from bottom wall 12a of vessel 12. Less energy is therefore required due to the relatively shallow submersion of said diffuser.

Outer tube 24 is co-axial with inner tube 14 and has a diameter of sufficient dimension to receive said inner tube 14 and diffuser 22 within its lumen.

The depth of diffuser 22 may be adjusted. In some applications it may be near the surface of the liquid culture media as depicted and in other applications it may be positioned at a deeper level. It is always within the lumen of outer tube 24.

Cap 26 surmounts the trailing end of outer tube 24, secures inner tube 14, and provides a mounting means for said outer tube so that said outer tube is suspended within vessel 12 with the lowermost, leading end of said outer tube being spaced apart from a bottom of said vessel. A plurality of circumferentially spaced openings 28 is formed proximate to said cap about its periphery.

Figure 3:
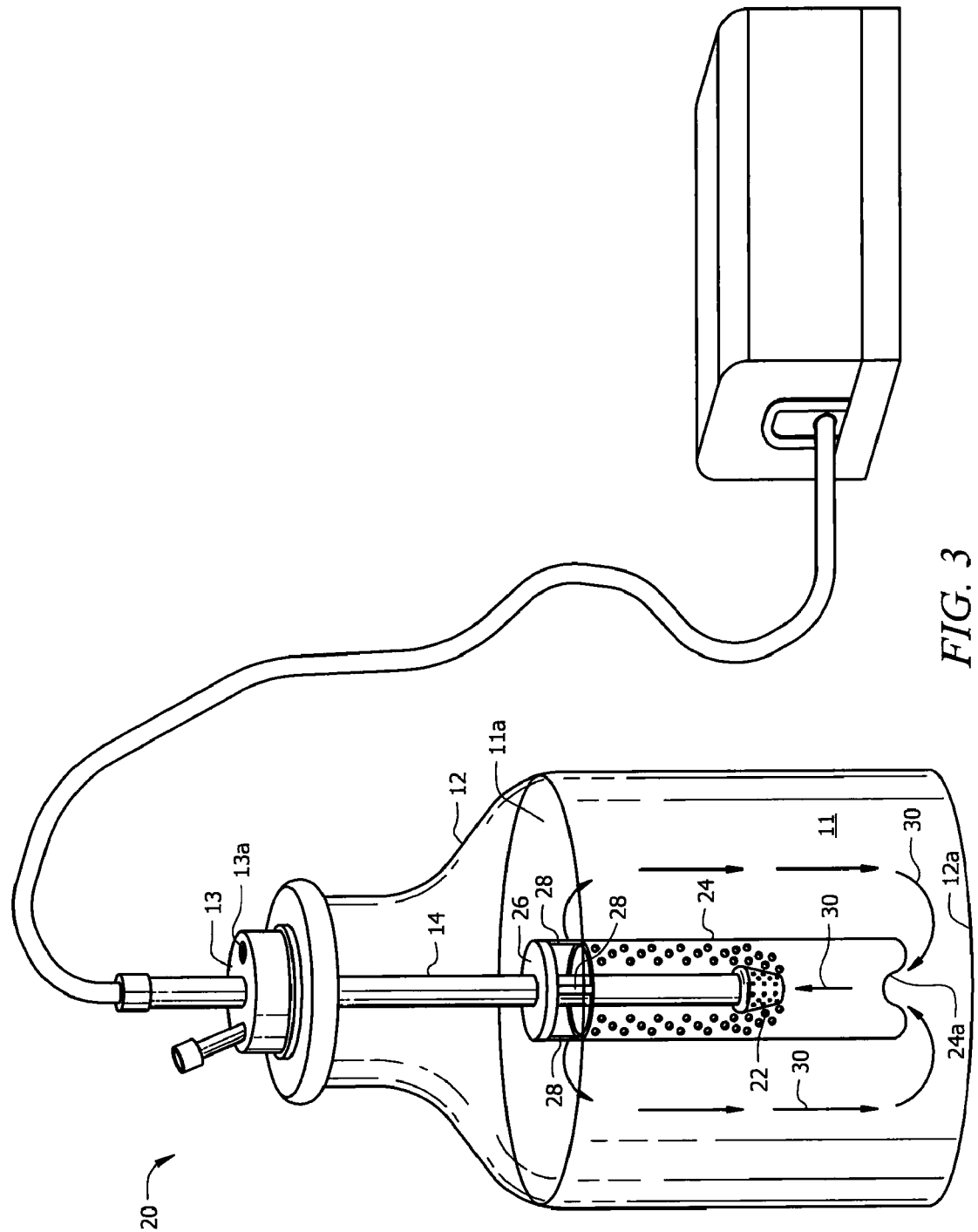
FIG. 3 is a front elevational view depicting the tubes of FIG. 2 when immersed in a liquid culture media.

As best understood in connection with FIG. 3, outer tube 24 is mounted within vessel 12 so that the lowermost end of cap 26 is flush with the surface of the liquid culture media. The lowermost ends of said openings 28 are therefore only slightly immersed within or substantially flush with said liquid culture media.

Circulating arrows, collectively denoted 30 in FIG. 3, indicate the toroidal path of travel of liquid within vessel 12 when the remote pump is operating. Air bubbles 16 escaping from diffuser 22 enter the lumen of outer tube 24 at its leading end 24a and flow upwardly in the lumen of outer tube 24 until they reach openings 28 formed in cap 26. The upwardly flowing air bubbles 16 entrain the liquid culture media 11 in their wake as said bubbles 16 flow upwardly. Accordingly, liquid culture media 11 flows upwardly in the lumen of outer tube 24, radially outwardly through openings 28 formed in cap 26, and downwardly outside of outer tube 24, back to open leading end 24a. This toroidal flow continues for as long as the remote pump is operating.

The upward flow of media 11 into the open bottom 24a of outer tube 24 is caused by a small vacuum created at open bottom 24a by the upward flow of bubbles 16 and the entraining of media that results. Once such upward flow is established, it continues without interruption as long as the remote pump is operating. When the pump is deactivated, the flow of air stops, no bubbles are emitted by diffuser 22, and the established flow coasts to an end.

In one embodiment of the invention, outer tube 24, inner tube 14 and diffuser 22 are constructed of acrylic. In another embodiment of the invention, outer tube 24, inner tube 14 and diffuser 22 are constructed of glass. An advantage of using glass is that the assembly may be autoclaved. In yet another embodiment of the invention, outer tube 24, inner tube 14 and diffuser 22 are constructed of polymer. An advantage of polymer construction is that the sterile assembly may be deployed as a disposable, one-time use product.

The novel toroidal mixing device is energy-efficient, inexpensive to manufacture, and achieves the required sparging, mixing, and circulation by means of infusion of gas that merges into a continuous toroidal flowing pattern that optimizes cell growth and high yields and otherwise meets all of the objects of the invention.

It will thus be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A device and a vessel, said device for circulating a liquid media in said vessel, comprising:
    a gas infusion tube having a leading end immersed in said liquid media and a trailing end adapted to be in fluid communication with a remote air pump that is external to said vessel;
    a diffuser secured to said leading end of said gas infusion tube;
    an outer tube having a lumen of sufficient diameter to receive therewithin said gas infusion tube and said diffuser;
    said outer tube having a leading end disposed in spaced apart relation to a bottom wall of said vessel and having a trailing end substantially flush with a surface of said liquid media;
    a plurality of circumferentially spaced openings formed proximate said cap;
    said diffuser forming bubbles in said liquid media that flow upwardly through the lumen of said outer tube, entraining said liquid media so that said liquid media follows a path of travel flowing upwardly through said lumen of said outer tube;
    said upwardly flowing liquid media changing direction a first time and flowing radially outwardly at the surface of said liquid media through said circumferentially spaced openings;
    said radially outwardly flowing liquid media changing direction a second time and flowing downwardly, externally of said outer tube;
    said downwardly flowing liquid media changing direction a third time and being entrained by said upwardly flowing bubbles into said leading end of said outer tube and thereafter repeating said path of travel;
    said path of travel being toroidal; and
    said path of travel ensuring that the liquid media is thoroughly mixed.

2. The device of claim 1 wherein said gas infusion tube, diffuser and outer tube are constructed of acrylic.

3. The device of claim 1 wherein said gas infusion tube, diffuser and outer tube are constructed of polymer.

4. The device of claim 1 wherein said gas infusion tube, diffuser and outer tube are constructed of glass.

5. The device of claim 4 wherein said diffuser is constructed of frittered glass.

6. A device and a vessel, said device for circulating a liquid media in said vessel, comprising:
    said vessel having an opening at an uppermost end thereof;
    a stopper positioned in said opening;
    a gas infusion tube having a leading end immersed in said liquid media and a trailing end adapted to be in fluid communication with a remote air pump that is external to said vessel;
    at least one bore formed in said stopper;
    said gas infusion tube extending through said at least one bore, said stopper thereby providing a mounting means for suspending said gas discharge tube within a hollow interior of said vessel;
    a diffuser secured to said leading end of said gas infusion tube;
    an outer tube having a lumen of sufficient diameter to receive therewithin said gas infusion tube and said diffuser;
    said outer tube having a leading end disposed in spaced apart relation to a bottom wall of said vessel and having a trailing end substantially flush with a level of said liquid media;
    a cap secured to said outer tube at a trailing end of said outer tube;
    an aperture in said cap slidably receiving said gas infusion tube and aligning, said gas infusion tube in axial relation to said outer tube; and
    a plurality of circumferentially spaced openings formed proximate to said cap;
    said diffuser forming bubbles in said liquid media that flow upwardly through the lumen of said outer tube, entraining said liquid media so that said liquid media follows a path of travel flowing upwardly through said lumen of said outer tube;
    said upwardly flowing liquid media changing direction a first time and flowing radially outwardly at the surface of said liquid media through said circumferentially spaced openings;

said radially outwardly flowing liquid media changing direction a second time and flowing downwardly, externally of said outer tube;

said downwardly flowing liquid media changing direction a third time and being entrained by said upwardly flowing bubbles into said leading end of said outer tube and thereafter repeating said path of travel;

said path of travel being toroidal; and said path of travel ensuring that the liquid media is thoroughly mixed.

7. The device of claim 6 wherein said gas infusion tube, diffuser and outer tube are constructed of acrylic.

8. The device of claim 7 wherein said diffuser is constructed of frittered glass.

9. The device of claim 6 wherein said gas infusion tube, diffuser and outer tube are constructed of polymer.

10. The device of claim 6 wherein said gas infusion tube, diffuser and outer tube are constructed of glass.

\* \* \* \* \*